(12) United States Patent
Weber et al.

(10) Patent No.: US 9,194,770 B2
(45) Date of Patent: Nov. 24, 2015

(54) SAMPLE SPLITTER

(71) Applicant: Mettler-Toledo AG, Greifensee (CH)

(72) Inventors: Christoph Weber, Pfäffikon (CH);
Marcel Trüb, Winterthur (CH); Manuel Schlegel, Wangs (CH); Amadeo Vergés, Bonstetten (CH)

(73) Assignee: Mettler-Toledo AG, Greifensee (CH)

( * ) Notice: Subject to any disclaimer, the term of this patent is extended or adjusted under 35 U.S.C. 154(b) by 200 days.

(21) Appl. No.: 13/940,631

(22) Filed: Jul. 12, 2013

(65) Prior Publication Data
US 2014/0026684 A1 Jan. 30, 2014

(30) Foreign Application Priority Data

Jul. 26, 2012 (EP) ..................................... 12178018

(51) Int. Cl.
*G01N 1/02* (2006.01)
*G01N 35/10* (2006.01)
*G01N 1/18* (2006.01)

(52) U.S. Cl.
CPC .................. *G01N 1/02* (2013.01); *G01N 35/10* (2013.01); *G01N 35/1065* (2013.01); *G01N 35/1095* (2013.01); *G01N 1/18* (2013.01)

(58) Field of Classification Search
None
See application file for complete search history.

(56) References Cited

U.S. PATENT DOCUMENTS

| | | | |
|---|---|---|---|
| 3,427,135 A | 2/1969 | Pelavin et al. | |
| 3,848,633 A | 11/1974 | Hurtig et al. | |
| 5,303,598 A | 4/1994 | Binder et al. | |
| 8,312,780 B2 | 11/2012 | Blacklin et al. | |
| 8,365,617 B2 | 2/2013 | Blacklin et al. | |
| 2005/0277199 A1 | 12/2005 | Isbell et al. | |
| 2006/0188407 A1* | 8/2006 | Gable et al. .................. | 422/100 |
| 2015/0167442 A1* | 6/2015 | Harfoushian ................. | 166/264 |

* cited by examiner

Primary Examiner — Andre Allen
(74) Attorney, Agent, or Firm — Standley Law Group LLP

(57) ABSTRACT

A device for splitting a sample, in particular a time-inhomogeneous sample, into two or more representative fractional samples, as well as a sample taking system with a sample splitter and a sample taker, wherein the sample splitter has a first pump (1, 201, 301) with a first flow rate and at least one second pump (2, 202, 302; 215) with a second flow rate, wherein the first pump and the at least one second pump (2, 202, 302; 215) co-act, so that the inhomogeneous sample on its passage through a conduit system (3, 203, 303) is at the same time split up into at least two representative fractional samples.

19 Claims, 3 Drawing Sheets

SAMPLE SPLITTER

CROSS-REFERENCE TO RELATED APPLICATIONS

This application is entitled to benefit of a right of priority under 35 USC §119 from European patent application 12178018.3, filed 26 Jul. 2012, the content of which is incorporated by reference as if fully recited herein.

TECHNICAL FIELD

The invention concerns a sample splitter and a method of splitting a sample into at least two representative fractional samples.

BACKGROUND

The process of splitting or dividing a sample into at least two representative fractional samples is used for example when a primary sample which has been taken or collected from a medium is prepared for further processing and/or analysis. The fractional samples can be subjected for example to different chemical, biological and/or physical analyses or can be further processed in different ways.

The term "primary sample" as used in the present context means any defined partial quantity which has been taken directly out of a medium. Consequently, the primary sample has the same properties as the medium at the time of taking the primary sample. Primary samples are taken for example from chemical, physical, biological, microbiological, pharmaceutical and/or food-engineering processes for analysis and/or further processing. A primary sample can further be taken from any other medium in liquid, gaseous, solid or mixed-phase form, brought into a suitable condition if desired, and subsequently analyzed. The primary sample as well as the medium can be liquid, gaseous and/or solid.

The term "sample" is used here in general for the quantity that is being split into one or more fractional samples. Accordingly, what is called a "sample" can be the primary sample as well as a processed and/or diluted primary sample.

The sample and/or the fractional samples are "representative" of the medium, which means that they have chemical and physical properties that are correlated directly with those of the medium, so that by analyzing the sample or fractional sample it is possible to determine, or at least draw conclusions about, the properties of the medium. Such a sample or fractional sample is hereinafter also referred to as "representative sample" or "representative fractional sample".

Based on the sample or a fractional sample that originated from it, one can determine for example the composition, physical or chemical parameters of the medium or the concentration of one or more components of the medium, or keep track of the course of a reaction or of the manufacturing process of a product, to name only a few examples.

Certainly the best known of these procedures is the manual separation of an essentially uniform primary sample into two or more fractional samples that share essentially the same properties and the same composition. The individual fractional samples can contain equal or different quantities of the primary sample. Thus, the sample can be split symmetrically or asymmetrically into at least two fractional samples. In practice, a primary sample is taken out of a medium that is located in a container or in an environment; the primary sample may be bought into a suitable condition if desired and then split manually into fractional samples. Depending on the properties of the sample, the splitting into fractional samples can be performed through volumetric and/or gravimetric processes.

Besides a purely manual procedure, it is also possible to divide a sample in a partially or totally automated way. The known state of the art offers a variety of devices that are suitable for this purpose, such as for example multi-channel pipettes or volumetric and/or gravimetric dosage-dispensing systems.

Common to both the manual and the automated way of splitting a sample is the fact that the primary sample is first collected, i.e. removed from its original environment, and is split only afterwards and often under different conditions. However, this is viable especially for media which change either not at all or only insignificantly after the sample has been taken out of the medium, so that the primary sample or the fractional sample still represents a "true copy" of the medium also in the subsequent analysis and has essentially the same properties as the medium. Samples of media that change rapidly should therefore be taken and split under known conditions, for example in a glove box with controllable environmental parameters.

The splitting of a sample into a plurality of fractional samples as described above has its limitations in the splitting of small samples, with media of non-uniform composition such as for example a liquid sample with solid components, and/or if a sample is to be split essentially without changing the environment.

Problems of this kind occur for example with small production quantities and/or in the laboratory within the realm of research and development. Examples are found in the fields of process development and/or research in so-called laboratory reactors which can have reaction volumes of a few milliliters up to several liters and are quite small in comparison to process systems of a magnitude up to several ten thousand liters. When taking a sample, the latter should be as small as possible in comparison to the medium quantity that is present, while still being representative and sufficiently large for a subsequent split and analysis. Especially in cases where the reaction volumes are small, these criteria can be met only with difficulty. The taking of a sample from a container, specifically a laboratory reactor, can be accomplished for example with an apparatus and/or a method as described in US 2011/0318243 A1 or US 2011/0314900 A1, wherein a primary sample is taken, a reaction that may be currently in progress is stopped directly at the capturing element for the sample collection by adding a suitable quenching medium to the primary sample, and wherein the sample can subsequently be flushed out of the capturing element with a suitable rinsing medium. This approach for taking a sample is suitable not only for liquid samples but also in particular for media that range from liquid to viscous, for slurries, and also for some solid media of a free-flowing consistency, i.e. media consisting essentially of pourable solids. Media or samples of a non-uniform composition are also often referred to as "inhomogeneous".

With the use of a rinse or purge medium, the volume of the sample increases in comparison to the primary sample. The primary sample is diluted. Depending on how well the primary sample mixes with the rinse medium, the primary sample and the rinse medium together can form a sample whose composition is uniform or changes over the duration of the rinsing. A sample whose composition changes over time can also come from a very fast-reacting medium and/or with continuous sample collection. A sample whose composition changes in time is hereinafter also referred to as a "time-inhomogeneous" sample.

The aforementioned manual way of splitting a sample can be used with a homogeneous sample as well as with a time-inhomogeneous sample, as the entire sample together with the rinse medium is completely removed from the environment of the medium and is further split only afterwards.

In contrast, an automated splitting of the sample into representative fractional samples can be performed in this manner only with a sample that is essentially uniform, in particular remaining uniform over time, or time-homogeneous. A time-inhomogeneous sample can thus be split only into chronologically defined fractional samples, wherein each of the fractional samples holds only a time-delimited segment of the composition of the time-inhomogeneous sample. Fractional samples of this kind occur for example when separating a sample chromatographically.

Consequently, the task presents itself to provide an apparatus as well as a method for splitting a sample, whereby a sample with a composition that varies over time can be split into two or more representative fractional samples.

SUMMARY

For a flowable sample, this capability is provided by a sample splitter for further splitting a sample into at least two fractional samples. The sample splitter comprises a conduit system with at least one conduit and at least one outlet for the delivery of the fractional samples, a sample chamber for the inhomogeneous sample which is connected to the conduit system and has an inlet for the sample, a first pump with a first flow rate and at least a second pump with a second flow rate, wherein the first and second pumps move or convey the sample through the conduit system. The first and the at least one second pump operate in a co-acting manner, so that on its passage through the conduit system the inhomogeneous sample is split at the same time into at least two representative fractional samples.

The sample splitter according to the invention provides the capability to divide different kinds of samples into representative fractional samples. The flowable sample can be a liquid or it can contain solid components. It is likewise possible to divide samples of flowable solids or samples containing a mixture of solids.

In particular, it is also possible with the sample splitter according to the invention to divide a time-inhomogeneous sample into at least two representative fractional samples.

The pumps are set to work together in a volumetrically synchronized way and can therefore split the sample into at least two fractional samples in such a way that the sample and the fractional samples ideally have the same composition. In particular, the first and the second pump have the same delivery stroke. The term "delivery stroke" refers to the timing cycle of a pump, and the flow rate is the quantity that is moved by a pump per delivery stroke. The volume of an individual fractional sample can be determined on the one hand by the flow rate of the respective pump and/or by the ratio of the cross-sections in the conduit system. The volumes of the fractional samples can be set through an appropriate selection of the pumps, wherein the ratios between the volumes of the fractional samples correspond to the ratios between the flow rates of the respective pumps, if the conduit system has a uniform cross-section. It is further possible to use conduits with different cross-sections which can result in an asymmetric splitting of the sample when pumps with equal flow rates are used. Of course, it is also possible that the sample splitter comprises pumps with different flow rates as well as conduits with different cross-sections. Accordingly, with an appropriate selection of the flow rates of the pumps or of the cross-sections of the conduit system, a sample, and in particular a time-inhomogeneous sample, can thus be split into at least two representative fractional samples.

The representative fractional samples and also the sample itself are of essentially equal composition. The term "equal composition" in this context refers to the chemical composition of the sample and/or the fractional samples and should be understood in the sense that the sample and the fractional samples would, within the range of uncertainty of a chemical, physical or biological analysis, deliver equal results. A sample or fractional sample is representative of the medium from which either the sample itself or a primary sample on which the sample is based was taken and has chemical and physical properties that correlate directly with those of the medium, so that from an analysis of the sample or fractional sample, it is possible to determine the properties of the medium or at least to draw conclusions about them.

The sample splitter comprises a first and at least one second pump that work synchronously in step with each other. The sample splitter can comprise a plurality of second pumps with equal or different flow rates. As it passes through the conduit system, the inhomogeneous sample is preferably split into a number of representative fractional samples that is equal to the number of pumps. Each fractional sample can be generated with a separate pump. Of course, the number of fractional samples also depends on the size or the volume of the sample itself and on the nature of the intended further processing of the individual fractional samples and is limited in particular by the minimum quantities that are required in the different methods of analysis to which the fractional samples will be subjected.

The first pump can be configured as a unidirectional or bidirectional pump. The at least one second pump is preferably a bidirectional pump. A unidirectional pump can move the sample only in one direction through the conduit system, while a bidirectional pump can aspirate the sample as well as expel it and therefore can move the sample in two directions through the conduit system.

In a preferred embodiment, the sample chamber is arranged between the first pump and the at least one outlet of the conduit system, and the first pump is configured as a unidirectional pump, so that it can move the medium only from the sample chamber through the conduit system to the outlet. This arrangement is very advantageous, as the first pump will thus not come directly into contact with the sample and accordingly cannot become contaminated by the sample.

The first pump in a further embodiment can be configured as a bidirectional pump, which is particularly advantageous to achieve a better mixing of the sample in the sample chamber, and also for the cleaning of the sample chamber with a cleaning agent pumped into the sample chamber by the first pump.

The at least one second pump can have a flow rate different from the first pump. Further embodiments of the sample splitter can also have a first and at least one second pump with equal flow rates. The sample splitter can have a plurality of second pumps with equal or different flow rates.

The ratio between the volumes of the fractional samples correlates with the flow rates of the respective pumps, particularly if the conduit system has a uniform cross-section, i.e. if all conduits of the conduit system have the same cross-section. If pumps with equal flow rates are used, the sample will be split into fractional samples of equal volume. On the other hand, if pumps with different flow rates are used, the sample can be split asymmetrically into fractional samples with different volumes. Independent of the volume ratios of the fractional samples relative to each other, a sample splitter according to the invention has the capability to produce representative fractional samples.

The pumps are preferably employed as a first pump and/or at least one second pump which can be volumetrically synchronized. It is particularly preferred to use pumps of identical design which differ only in their respective flow rates, so as to influence the splitting of the sample into fractional samples as little as possible. The types of pumps that can be used include for example swash plate pumps or metering pumps.

The sample splitter can be a stand-alone unit, or it can also be tied into a system or connected to a system in which the medium is located from which the sample is taken.

In a further embodiment, the conduit system of the sample splitter according to the invention can have a first conduit between the first pump and the sample chamber, a second conduit between the sample chamber and the at least one outlet, and at least a third conduit between the at least one second pump and the at least one outlet, wherein the conduits have uniform cross-sections.

As an alternative, the conduit system of the sample splitter according to the invention can comprise a first conduit between the first pump and the sample chamber, a second conduit between the sample chamber and the at least one outlet, and at least a third conduit between the at least one second pump and the at least one outlet, wherein at least the second and the third conduit have different cross-sections.

Through the selection of the ratios between the cross-sections of the second and the at least one third conduit and the at least one outlet, the ratio between the volumes of the at least two fractional samples can be influenced. This is of particular advantage if for example pumps of the exact same design with identical delivery stroke and identical flow rate are employed, or also as a way to set a volume ratio which, due to technical constraints, could not be realized through the selection of the pumps alone.

In addition, the conduit system can have at least one further inlet serving as a supply line for one or more rinse media, a quench medium and/or other substances for the conditioning of the sample. Thus, the sample can for example be diluted, quenched or otherwise chemically treated or conditioned directly in the conduit system, preferably in the sample chamber. The term "conditioning" is used here in a general sense for a treatment of the sample with at least one further substance.

The sample chamber can be a separate element as well as a conduit section of the conduit system. Depending on the field of application, the conduit system can consist of pipe sections or hose sections that are connected to each other.

In a further example of an embodiment, at least one outlet of the conduit system can be connected to a sample receptacle or sample container, a sample rack or an analyzer. Thus, the fractional samples can either be analyzed directly with the connected analyzer, or they can be dispensed into a suitable individual sample receptacle or into a sample receptacle in a sample rack. The sample rack is preferably of a configuration that facilitates the manual or automated filling of a large number of sample receptacles. Such sample racks are available from different suppliers for example in the form of linear sample racks or sample carousels.

The analyzer can for example be an HPLC (high performance liquid chromatography) analyzer, a gas-chromatography analyzer, a mass spectrometer, an infrared-, near-infrared-, UV/VIS-, or Raman spectrometer, an NMR (nuclear magnetic resonance) spectrometer, or another instrument that is suitable for the analysis of the fractional sample.

The sample splitter according to the invention, in conjunction with a sample collector or sample taker for taking a primary sample from a medium can be part of a sample taking system for the splitting of a sample, in particular a time-inhomogeneous sample, into at least two fractional samples.

The sample splitter as part of the sample taking system comprises a conduit system with at least one conduit, a first pump with a first flow rate and at least a second pump with a second flow rate.

The sample taker comprises a sample chamber for the inhomogeneous sample. The sample chamber comprises at least one inlet conduit and at least one outlet conduit and is connected by way of the outlet conduit to the conduit system of the sample splitter.

The first and the at least one second pump work together in a volumetrically synchronous way, so that while the sample is passing through the conduit system, it is split at the same time into a plurality of representative samples.

The sample taking system can further comprise a housing and an element that is slidable along a linear path, wherein the linearly slidable element is movably supported in the housing and wherein the sample chamber is arranged at one end of the linearly slidable element, so that by shifting the linearly slidable element the sample chamber can introduced into or retracted from a medium.

With this arrangement, a primary probe can be taken from the medium with the sample taker. If necessary, the sample can be conditioned or diluted in the sample chamber, whereupon the sample can be delivered directly to the sample splitter, so that within a short time of taking a sample the latter can be split into at least two fractional samples. The sample chamber is preferably configured at least partially open, so that when the chamber is being moved into the medium it can take up a sample which is subsequently locked into the sample chamber in the housing of the sample taker when the linearly slidable element is retracted.

The first pump can preferably serve to take a primary sample from the medium as well as, in cooperation with the synchronously working second pump, to divide the inhomogeneous sample into two fractional samples. The first pump can be a unidirectional or a bidirectional pump.

Further embodiments of the sample taking system comprise the possibility of bringing at least one further substance by way of the at least one inlet conduit into the sample chamber, if the latter is enclosed in the housing, so that the primary sample can be quenched, diluted or otherwise conditioned directly in the sample chamber. For this purpose, the sample chamber can be connected to one or more supply reservoirs containing the respective substances.

Depending on the nature and consistency of the medium, a rinse agent can be delivered by way of an inlet conduit into the sample chamber. The rinsing agent can be used to move the sample from the sample chamber into the conduit system of the sample splitter and/or to clean the sample chamber before taking a new sample.

The sample taking system comprises a sample splitter according to the invention which can have any of the configurations of the foregoing description.

A method of splitting an inhomogeneous sample into at least two representative fractional samples by means of a sample splitter according to the invention comprises the following steps: starting up the first and the second pump so that they work together in a volumetrically synchronized way; introducing a sample into the conduit system and splitting the sample by means of the synchronously operating pumps into a first and a second representative fractional sample.

The method further comprises an additional step in which at least one of the fractional samples is brought directly into an analyzer that is connected to the sample splitter.

BRIEF DESCRIPTION OF THE DRAWINGS

Different examples of embodiments of a sample splitter according to the invention and of a sample taking system with a sample splitter according to the invention will be described in detail with references to the attached drawings, wherein identical elements carry the same or similar reference symbols, and wherein.

DETAILED DESCRIPTION

Figure 1:
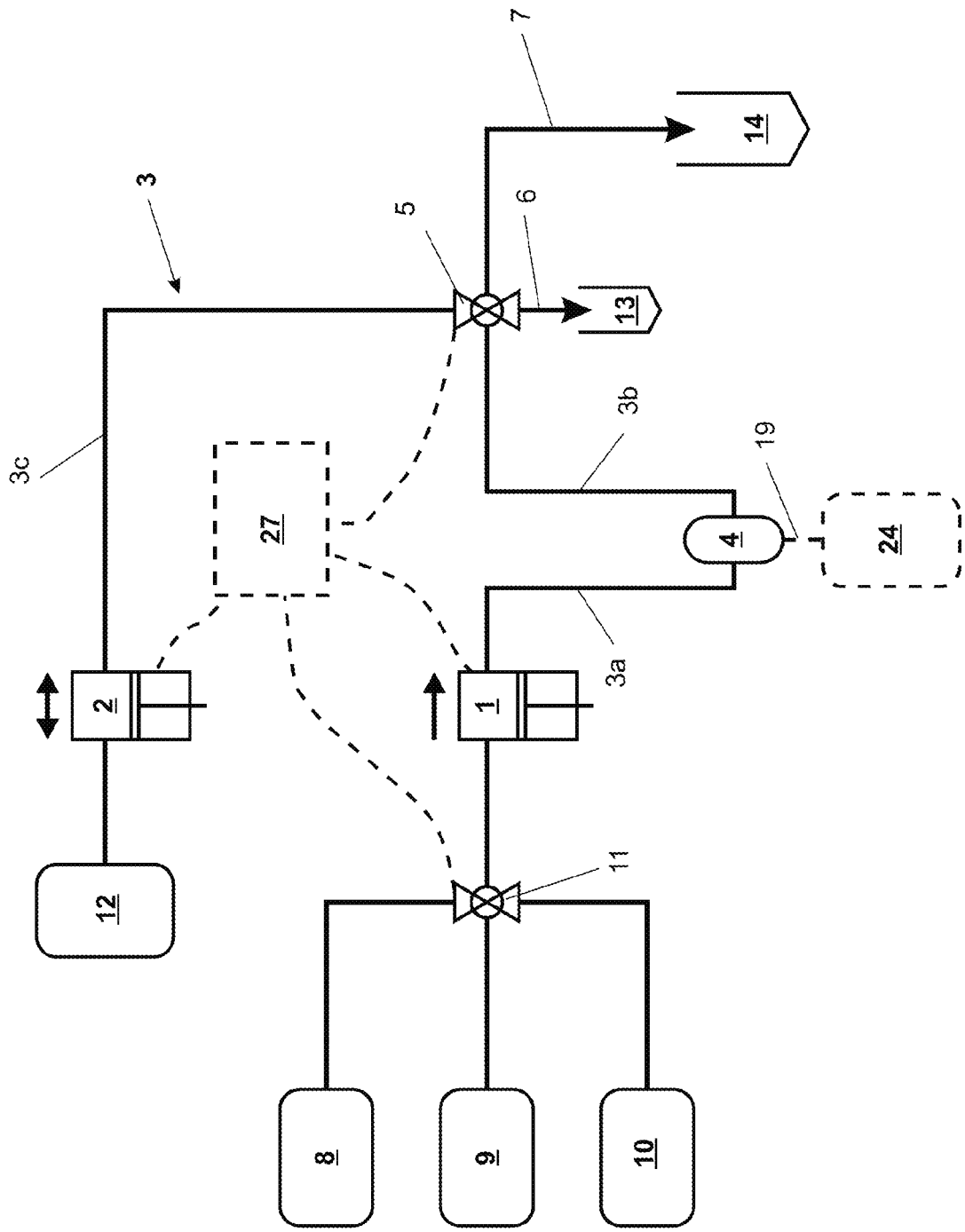
FIG. 1 is a schematic depiction of a sample splitter with two pumps.

FIG. 1 schematically illustrates a sample splitter with a first pump 1 and a second pump 2 which are connected to a conduit system 3.

The first pump 1 in this example is a unidirectional pump, as indicated by the arrow, and has a first flow rate. The first pump 1 can propel or move a medium only in one direction.

The sample splitter further comprises a sample chamber 4 which is connected to the conduit system 3 and has at least one inlet for the intake of an inhomogeneous sample. The inlet can for example be an opening in the sample chamber 4 or, as indicated in FIG. 1, a connecting passage 19 to a further conduit or any kind of vessel 24 holding a medium from which an inhomogeneous primary sample can be taken. The sample, more specifically the primary sample, is preferably moved directly from the vessel 24 into the sample chamber 4, but can also be brought manually into the sample chamber 4.

The sample chamber 4 is arranged between the unidirectional first pump 1 and an outlet valve 5. Furthermore, the second pump 2 as well as two outlets 6, 7 are connected through the conduit system 3 to the outlet valve 5. The outlet valve 5 is configured in this case as a multiport valve and can connect the sample chamber 4 and the second pump 2 to the first outlet 6 or to the second outlet 7.

The conduit system 3 comprises at least a first conduit 3a which is arranged between the first pump 1 and the sample chamber 4, a second conduit 3b which is arranged between the sample chamber 4 and the outlet valve 5, and a third conduit 3c which is arranged between the second pump 2 and the outlet valve 5. The second and third conduits 3b, 3c can have equal or different cross-sections. The use of different cross-sections has an influence on the volume ratio of the at least two fractional samples.

The second pump 2 is a bidirectional pump with a second flow rate, which can move the sample in the conduit system 3, primarily in the first and second conduits 3a, 3b, in both directions, as is indicated by the arrow. The first and second pumps 1, 2 can be operated to co-act in a volumetrically synchronized, i.e. simultaneous, way and thus split the sample into representative fractional samples.

There can further be one or more reservoirs or reservoir containers 8, 9, 10, three in this example, which contain reagents for the conditioning of the sample, such as quenching or thinning agents, or substances for the cleaning of the sample splitter.

The reservoirs 8, 9, 10 are connected to the conduit system 3 by way of a further valve 11 and are thus placed upstream of the first pump 1, so that the contents of the containers can be injected by way of the conduit 3a into the conduit system 3, whereby the sample, more specifically the primary sample in the sample chamber 4, can be conditioned or the sample chamber 4 and/or the conduit system 3 can be rinsed and/or cleaned.

Furthermore, the conduit system 3 of the sample splitter can also be supplied with a gas or a protective gas from one of the reservoirs 8, 9, 10. Introducing of a gas can be used for example to saturate the sample with the gas or also to dry out the entire conduit system 3. The gas can further be a protective or inert gas which is used before the sample is brought in, for example to drive oxygen out of the conduit system 3 in order to prevent oxidation of the sample in the sample chamber 4.

A further reservoir 12 can be put ahead of the second pump 2. The reservoir 12 preferably holds a cleaning agent, so that the second pump 2 and/or the conduit between the second pump 2 and the outlet valve 5 and/or the outlets 6, 7 can be cleaned.

To divide a sample, a primary sample or a sample is first brought into the sample chamber 4, where it can be conditioned with agents from the reservoirs 8, 9, 10. These agents are moved by means of the first pump 1 into the sample chamber 4. After the sample has been conditioned, it is moved by the first pump 1 from the sample chamber 4 into the second conduit 3b and simultaneously moved by the second pump 2 into the third conduit 3c, so that the sample is split up at the outlet valve 5 into two representative fractional samples, one of which leaves the conduit system 3 through one of the outlets 6, 7 while the other can be moved into the third conduit 3c and, in a further step, can be moved out of the conduit system 3 by means of the second pump 2. The first and second pumps 1, 2 run in a volumetrically synchronized way and can have equal or different flow rates. The two pumps 1, 2 can for example be swash plate pumps or metering pumps.

The sample is now split into two representative fractional samples of equal composition when the outlet valve 5 connects the two pumps 1, 2 and the first outlet 6 to each other. Due to the synchronous operation of the two pumps 1, 2, a first part of the sample is discharged from the conduit system 3 through the first outlet 6 as the first fractional sample, and a second part, i.e. the second fractional sample, is moved into the third conduit 3c between the second pump 2 and the outlet valve 5. The third conduit 3c is preferably configured in such a way that its volume is large enough to accommodate the second fractional sample without the latter coming into contact with the second pump 2.

As soon as the first fractional sample has left the conduit system 3 by way of the outlet 6 and has for example been brought into the first receptacle 13 shown in FIG. 1, the outlet valve 5 can be switched to the second outlet 7, and the second fractional sample can be brought to the second receptacle 14 by way of the outlet 7, as the second pump 2 is switched over and now expels the fractional sample from the conduit system 3.

The two pumps 1, 2 as well as of the valves 11, 5 are controlled by a controller unit 27 as indicated in FIG. 1.

In this way a sample can be split into two representative fractional samples, both of which have essentially the same composition as the sample. As the two pumps 1, 2 operate in a volumetrically synchronous manner, even a time-inhomogeneous sample can be split into two representative fractional samples, as the sample is split up continuously at the outlet valve 5. The fractional samples have the same composition as the sample and duplicate the time distribution of the sample substance in the sample. The fractional samples as well as the sample itself are representative of the medium.

The volume ratio of the two fractional samples relative to each other is determined by the ratio of the respective flow rates of the first and second pumps 1, 2 and/or the ratio of the cross-sections of the second and third conduits 3b, 3c. In this way, a sample of e.g. 10 ml can be split into two fractional samples of 5 ml each, if the flow rates and the cross-sections are equal, or into a fractional sample of 2 ml and another of 8 ml, if the flow rates or the cross-sections are in a ratio of 1:4 to each other. Of course, at least one of the fractional samples can be further split in a following step. Based on the selection of the first and second pump and/or the cross-sections of the second and third conduits 3b, 3c, the sample splitter can thus split a sample into a plurality of fractional samples of equal or different volumes according to what is most advantageous for the user and/or for a subsequent analysis. This is of particular benefit for the preparation of analysis samples, as it provides for example the capability to directly split samples that are collected automatically from a process into representative fractional samples with suitable volumes.

Figure 2:
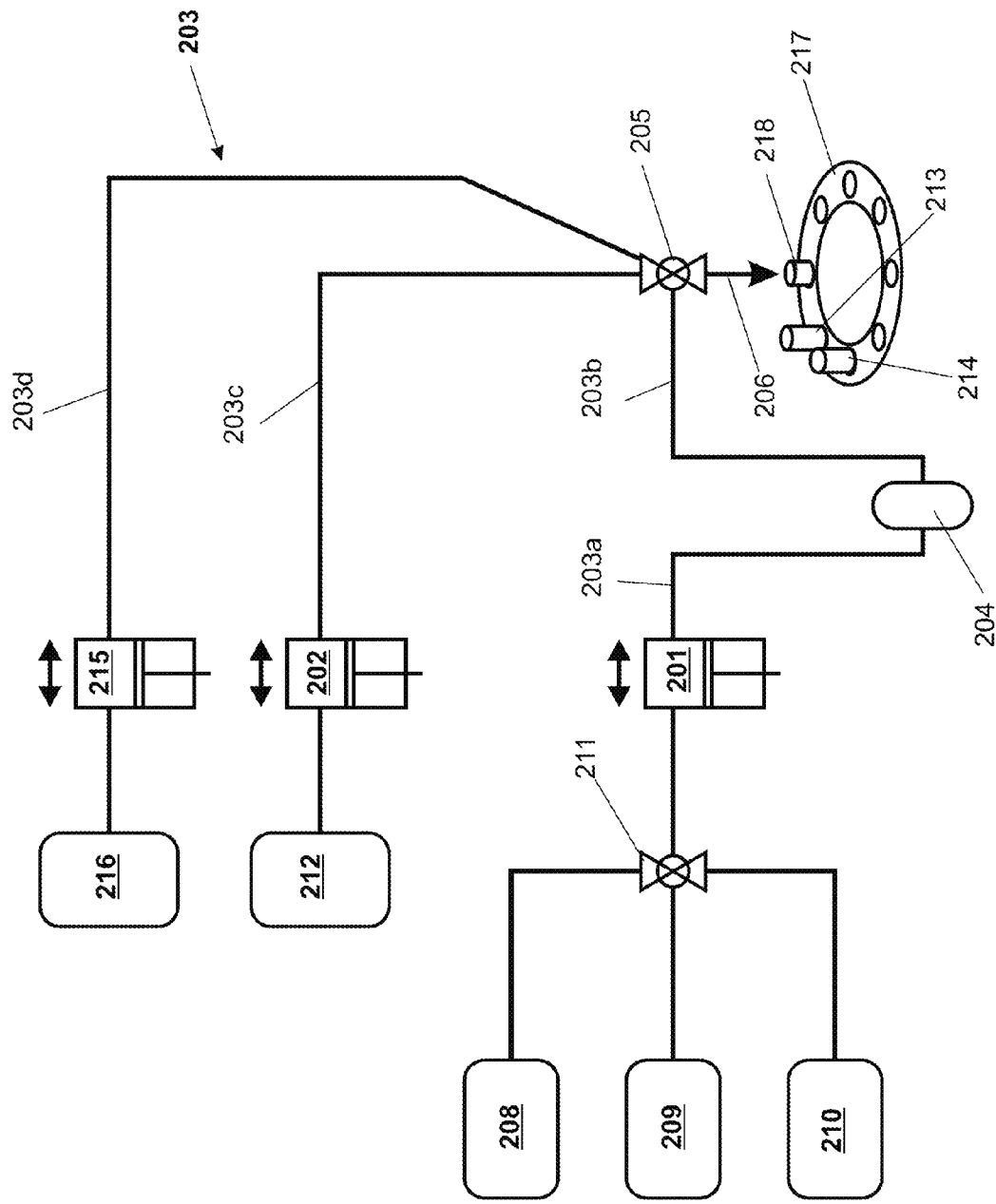
FIG. 2 is a schematic depiction of a sample splitter with three pumps.

FIG. 2 shows a further example of a sample splitter according to the invention which, in contrast to the embodiment of FIG. 1, has a third pump 215 with a further reservoir 216 and alternative containers to hold the fractional samples.

The first, second and third pumps 201, 202, 215 work in a volumetrically synchronized way, and all three of the pumps 201, 202, 215 in this example are configured as bidirectional pumps. The three pumps 201, 202, 215 can have equal or different flow rates.

The pumps 201, 202, 215 are connected by way of an outlet valve 205 to a single outlet 206. The outlet valve 205 is configured as a multiport valve. The outlet valve 205 can be switched to a position where all of the pumps 201, 202, 215 are connected to the outlet 206, or where only the second or third pump 202, 215 is connected to the outlet 206. As described already in the context of FIG. 1, a primary sample can be conditioned in the sample chamber 204 and split in this case into three fractional samples by means of pumps 201, 202, 215. The sample is moved by the first pump 201 through the second conduit 203b to the outlet valve 205 where the sample is being split, as a first fractional sample leaves the conduit system 203 through the outlet 206, the second fractional sample is moved into the third conduit 203c between the outlet valve 205 and the second pump 202, and the third fractional sample is moved into a fourth conduit 203d between the outlet valve 205 and the third pump 215. Next, the outlet valve 205 can be switched over, so that the second or third fractional sample in, respectively, the third or the fourth conduit 203c, 203d is discharged from the conduit system 203 by switching over the second or third pump 202, 215. Depending on the respective position of the outlet valve 205 corresponding with the discharge of the second or third fractional sample, only the corresponding pump is activated while the others are turned off, so that the remaining fractional sample is not moved into the pump.

To separate the three fractional samples from each other, a suitable sample rack 217 holding sample receptacles 213, 214, 218 for the three fractional samples is located at the outlet 206. The sample rack 217 makes it possible to set a suitable receptacle 213, 214, 218 into position to receive each of the fractional samples. The shifting of the sample rack 217, i.e. moving new sample receptacles 213, 214, 218 into position, can be performed manually or under automatic control. A variety of different sample holder frames, such as for example sample carousels or sample racks, are known in the laboratory sector. As an example, the sample receptacles 213, 214, 218 are shown here in different sizes, but of course they could also all be of the same size.

Instead of only one outlet 206, the sample splitter can of course also comprise a plurality of outlets which are assigned to at least one pump, as illustrated in FIG. 1.

Figure 3:
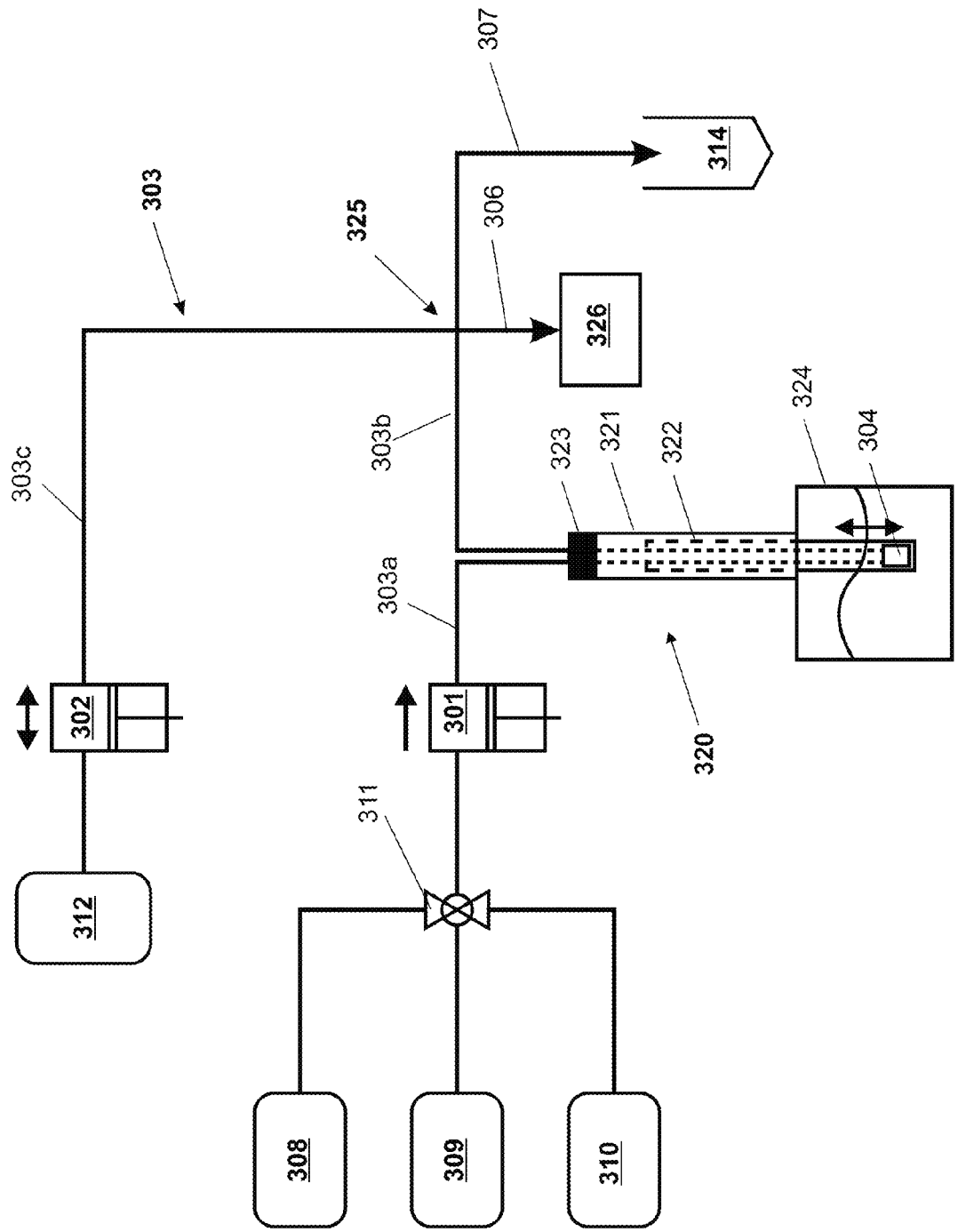
FIG. 3 is a schematic depiction of a sample taking system with a sample taker and with a sample splitter having two pumps.

FIG. 3 shows a sample taking system with a sample taker 320 and a sample splitter with two pumps 301, 302. Most of the elements of the sample splitter are analogous to those of the sample splitters shown in FIGS. 1 and 2, but in the case of FIG. 3 a sample chamber 304 is arranged in the sample taker 320. Furthermore, the sample splitter can deliver at least one of the fractional samples to an analyzer 326. The sample splitter is preferably configured in such a way that the volume of the fractional sample is matched to the analyzer 326 that is being used. The analyzer 326 can be any one of a multitude of instruments, for example an HPLC (high performance liquid chromatography) analyzer, a gas-chromatography analyzer, a mass spectrometer, an infrared-, near-infrared-, UV/VIS-, or Raman spectrometer, an NMR spectrometer, or another instrument that is suitable for the analysis of the fractional sample.

In contrast to the sample splitters shown in FIGS. 1 and 2, the sample splitter of FIG. 3 has no outlet valve. The two pumps 301, 302 are connected, respectively, by way of the second conduit 303b and the third conduit 303c directly to the outlets 306, 307 by way of a suitable connector element 325. In the operation of this sample splitter, a sample is moved by the first, unidirectional pump 301 from the sample chamber 304 to the connector element 325 where the sample is being split, as a first fractional sample is moved by the first pump 301 to one of the outlets 307, 306 and a second fractional sample is moved by the second pump 302 into the third conduit 303c between the second pump 302 and the connector element 303. When the first fractional sample has been delivered, the first pump 301 is switched off and the second pump 302 is switched over, so that the second fractional sample is now being moved to the selected outlet 307, 306.

For the separation of the fractional samples, one of the outlets 307, 306 can be closed as needed.

Of course, the sample splitter could also include a suitable multiport valve and/or only a single outlet as was previously described.

As has already been described above, the first pump 301 can be a unidirectional pump as shown here, or a bidirectional pump. The sample chamber 304 can be connected by way of the first conduit 303a and the first pump 301 to different reservoirs 308, 309, 310 holding substances for the thinning or conditioning of the primary sample and/or for the cleaning of the sample chamber 304. These reservoirs are preferably arranged upstream of the first pump 301, connected to the latter by way of a valve 311.

The sample taker 320 shown in FIG. 3 has a housing 321 in which a linearly slidable element 322 and a drive mechanism 323 are arranged. The element 322 can be moved out of, and back into, the housing 321 by means of the drive mechanism 323. As indicated here, the sample taker 320 is suitably connected to a vessel 324 which holds a medium, so that the element 322 can be introduced into and retracted from the medium and that a primary sample taken from the medium can be conditioned and/or diluted inside the sample chamber 304 which is enclosed in the housing 321, whereupon the sample can be split by the sample splitter into a number of representative fractional samples corresponding to the number of pumps. A sample chamber 304 which is tied into the conduit system 3 of the sample splitter is arranged at the end of the element 322 that comes into contact with the medium.

Although the invention has been described by presenting examples of specific embodiments, it is considered evident that numerous further variants could be created based on the teachings of the present invention, for example by combining features of the individual embodiments with each other and/or by interchanging individual functional units between the embodiments. In particular, a sample splitter according to the invention can be combined with different sample takers of the known state of the art. The sample splitter can be configured with or without an outlet valve. The fractional samples can be delivered into different containers, as mentioned in an example in the context of the drawings. Furthermore, the sample splitter can comprise a larger or smaller number of reservoirs than are shown here for conditioning and cleaning agents. The sample splitter can further comprise two or more pumps as well as a conduit system with conduits that have equal or different cross-sections, wherein the first pump can be configured as a unidirectional or a bidirectional pump, so that a sample can preferably be split into a number of representative fractional samples corresponding to the number of pumps.

What is claimed is:

1. A device for splitting a sample, in particular a time-inhomogeneous sample, into two or more fractional samples, the device comprising:
a sample chamber with an inlet through which the inhomogeneous sample is received;
a first pump having a first flow rate;
a second pump having a second flow rate, configured for bidirectional operation; and
a conduit system, having at least one conduit and at least one outlet, the at least one conduit connected to the sample chamber, the first pump and the second pump, so that the respective pumps, operating in a co-acting manner, move the sample from the sample chamber, split the sample into two or more representative fractional samples and deliver the two or more fractional samples to at least one of the at least one outlets.

2. The device of claim 1, wherein:
the first pump is configured for unidirectional operation.

3. The device of claim 2, wherein:
the first and second flow rates are different.

4. The device of claim 2, wherein:
the first and second flow rates are the same.

5. The device of claim 2, wherein:
the at least one conduit of the conduit system comprises:
a first conduit, arranged between the first pump and the sample chamber;
a second conduit, arranged between the sample chamber and the at least one outlet; and
a third conduit, arranged between the second pump and the at least one outlet.

6. The device of claim 5, wherein:
the conduits have uniform cross-sectional flow areas.

7. The device of claim 5, wherein:
at least the second and third conduits have cross-sectional flow areas that are different from each other.

8. The device of claim 1, wherein:
the sample chamber is arranged in the conduit system between the first pump and the at least one outlet.

9. The device of claim 1, further comprising:
at least one supply port in the conduit system to deliver at least one of: a rinse medium, a quench medium and another substance for the conditioning of the sample.

10. The device of claim 1, further comprising:
a sample rack, connected to one of the at least one outlets.

11. The device of claim 1, further comprising:
an analyzer, connected to one of the at least one outlets.

12. The device of claim 11, wherein:
the analyzer is selected from the group consisting of: an HPLC analyzer, a gas-chromatography analyzer, a mass spectrometer, an infrared-spectrometer, a near-infrared-spectrometer, a UV/VIS-spectrometer, a Raman spectrometer, and an NMR spectrometer.

13. The device of claim 1, wherein:
the at least one conduit of the conduit system comprises:
a first conduit, arranged between the first pump and the sample chamber;
a second conduit, arranged between the sample chamber and the at least one outlet; and
a third conduit, arranged between the second pump and the at least one outlet.

14. The device of claim 13, wherein:
the conduits have uniform cross-sectional flow areas.

15. The device of claim 13, wherein:
at least the second and third conduits have cross-sectional flow areas that different from each other.

16. A system for taking an inhomogeneous sample from a medium, comprising:
a sample splitter device according to claim 1; and
a device for taking the inhomogeneous sample from the medium, the sample chamber of the sample splitter device being arranged therein.

17. The system according to claim 12, wherein:
the device for taking the sample further comprises:
a housing; and
an element, supported in the housing with the sample chamber arranged thereon, such that sliding movement of the element along a linear path introduces the sample chamber into the medium and retracts the sample chamber therefrom.

18. A method of splitting a sample, in particular a time-inhomogeneous sample, into at least two representative fractional samples with a sample splitter according to claim 1, wherein the method comprises the following steps:
starting up the first and the second pump, so that they co-act in a volumetrically synchronous way;
introducing a sample into the sample chamber of the conduit system; and
splitting the sample by means of the synchronously operating first and at least one second pump into a first and at least one second representative fractional sample.

19. The method of claim 18, further comprising the step of:
delivering the first and the at least one second representative fractional sample directly into an analyzer that is connected to the sample splitter.

* * * * *